(12) United States Patent
Carr Pérez et al.

(10) Patent No.: US 6,429,295 B1
(45) Date of Patent: Aug. 6, 2002

(54) MONOCLONAL ANTIBODY WHICH RECOGNIZES THE OLIGOSACCHARIDE N-GLYCOLYLATED-GALACTOSE-GLUCOSE SIALIC ACID IN MALIGNANT TUMORS, AND COMPOSITION CONTAINING IT

(75) Inventors: Adriana Carr Pérez; Zaima Mazorra Herrera; Luis Enrique Fernández Molina; Ana Maria Vázquez López; Ailette Mulet Sierra; Rolando Pérez Rodríguez, all of Havana (CU)

(73) Assignee: Centro de Inmunologia Molecular (CIM) (CU)

( * ) Notice: Subject to any disclaimer, the term of this patent is extended or adjusted under 35 U.S.C. 154(b) by 0 days.

(21) Appl. No.: 09/402,521

(22) PCT Filed: Feb. 5, 1999

(86) PCT No.: PCT/CU99/00001

§ 371 (c)(1),
(2), (4) Date: Nov. 22, 1999

(87) PCT Pub. No.: WO99/40119

PCT Pub. Date: Aug. 12, 1999

(30) Foreign Application Priority Data

Feb. 5, 1998 (CU) .................................................. 22/98

(51) Int. Cl.$^7$ ............................................. C07K 16/30
(52) U.S. Cl. ............................. 530/387.5; 530/387.1; 530/391.3; 424/137.1
(58) Field of Search .......................... 530/387.1, 387.5, 530/387.7, 388.1, 388.8, 388.85, 391.1, 391.3, 391.7; 435/7.1, 7.21, 7.23; 424/130.1, 137.1, 138.1, 141.1, 152.1, 155.1, 156.1, 174.1, 181.1

(56) References Cited

U.S. PATENT DOCUMENTS 4,965,198 A * 10/1990 Yamasaki et al.
5,411,881 A * 5/1995 Matsuda et al.

FOREIGN PATENT DOCUMENTS

EP         0 657 471 A      6/1995

OTHER PUBLICATIONS

Kusano, A. et al. Immunocytochemical study on internalization of anti–carbohydrate monoclonal antibodies. Anticancer Research, 13: 2207–2212, 1993.*
Paul, W.E. Editor, Fundamental Immunology, Raven Press, New York, pp. 135–138, 1984.*
Asaoka, H. et al. Two chicken monoclonal antibodies specific for heterophil Hanganutziu–Deicher antigens. Immunology Letters, 32: 91–96, 1992.*
Mujoo, K. et al. Functional properties and effect on growth suppression of human neuroblastoma tumors by isotype switch variants of monoclonal antiganglioside GD2 antibody 14.18. Cancer Research, 49: 2857–2861, Jun. 1989.*
Goers, J. Immunochemical Techniques Laboratory Manual, Academic Press, New York, pp. 69–79, 1993.*
H. Ozawa et al., "Generation of murine monoclonal antibodies specific for N–glycolneuraminic acid–containing gangliosides," *Archives of Biochemistry and Physics*, vol. 294, No. 2, May 1, 1992, pp. 427–33; New York. NY.
A. Carr et al., "Differences in immunological behavior between NacGM3 and NGcGM3 gangliosides," *Biotecnologia aplicada*, vol. 14, No. 1, 1997, p. 48; La Habana, Cuba.
M. Alfonso et al., "Human anti–ganglioside monoclonal antibodies generated by in vitro immunization," *Biotecnologia aplicada*, vol. 14, No. 1, 1997, pp. 45–46; La Habana, Cuba.
I. Kawashima et al., "Characterization of ganglioside expression in human melanoma cells: Immunological and biochemical analysis," *Journal of Biochemistry*, vol. 114, No. 2, Aug. 1993, pp. 186–93; Tokyo, Japan.

* cited by examiner

*Primary Examiner*—Sheela Huff
*Assistant Examiner*—Larry R. Helms
(74) *Attorney, Agent, or Firm*—Lackenbach Siegel LLP

(57) ABSTRACT

The present invention is related with the field of immunology and human medicine, particularly with the generation and selection of a monoclonal antibody (Mab) that recognizes the N-glycolylated-galactose-glucose sialic acid olygosaccharide sequence presents in malignant tumors.

One of the objectives of this invention is to provide a Mab of the IgG1 type that has the characteristic of recognizing with high specificity N-glycolylated-galactose-glucose sialic acid olygosaccharide sequence presents in malignant tissues of breast, melanomas and tumors of the liver, stomach, colon, rectum and kidneys. It also has the capacity of producing direct cytolysis of the tumoral cells bearing the N-glycolylated-galactose-glucose sialic acid olygosaccharide sequence, thus can be used for the diagnosis and treatment of certain neoplasic diseases.

Another objective of the present invention is to provide the hybridoma producing the referred Mab as well as the pharmaceutical composition containing it, for the treatment of neoplasic diseases.

13 Claims, 14 Drawing Sheets

Figure 4 :

| Glycolipids | Structure | TLCi |
|---|---|---|
| LacCer | Galβ1-4GlcCer | - |
| Gangliotri | GalNeuAcβ4-Galβ1-4GlcCer | - |
| Gangliotetra | Galβ3- GalNeuAcβ4- Galβ1-4GlcCer | - |
| GM3 | NeuAcα2-3 Galβ1-4GlcCer | - |
| GM2 | GalNAcβ1-4(NeuAcα2-3) Galβ1-4GlcCer | - |
| GM1a | Galβ1-3 GalNAcβ1-4(NeuAcα2-3) Galβ1-4GlcCer | - |
| GD3 | NeuAcα2-8NeuAcα2- 3Galβ1-4GlcCer | - |
| GD2 | GalNAcβ1-4(NeuAcα2-8NeuAcα2-3) Galβ1-4GlcCer | - |
| GD1a | NeuAcα2-3 Galβ1-3 GalNAcβ1-4(NeuAcα2-3) Galβ1-4GlcCer | - |
| GD1b | Galβ1-3GalNAcβ1-4(NeuAcα2-8Neuacα2-3)Galβ1-4GlcCer | - |
| GT1b | NeuAcα2-3Galβ1-3GalNAcβ1-4(NeuAcα2-8Neuacα2-3)Galβ1-4GlcCer | - |
| NGcGM3 | NeuGcα2-3 Galβ1-4GlcCer | + |
| NGcGM2 | GalNAcβ1-4(NeuGcα2-3) Galβ1-4GlcCer | - |
| NGcGM1a | Galβ1-3 GalNAcβ1-4(NeuGcα2-3) Galβ1-4GlcCer | - |
| NGcGM1b | NeuGcα2-3 Galβ1-3GalNAcβ1-4Galβ1-4GlcCer | - |
| NGcGD3 | NeuGcα2-8NeuGcα2-3Galβ1-GlcCer | - |
| NGcGD1a | NeuGcα2-3 Galβ1-3 GalNAcβ1-4(NeuGcα2-3)Galβ1-4GlcCer | - |
| NGcGD1c | NeuGcα2-8NeuGcα2-3Galβ1-4GalNAcβ1-3Galβ1-4GlcCer | - |
| NGc Sialyl-Paragloboside | NeuGcα2-3Galβ1-4GlcNeuAcβ1-33Galβ1-4GlcCer | - |
| I SO₃-GalCer | HSO₃-3GalCer | - |

Figure 5:
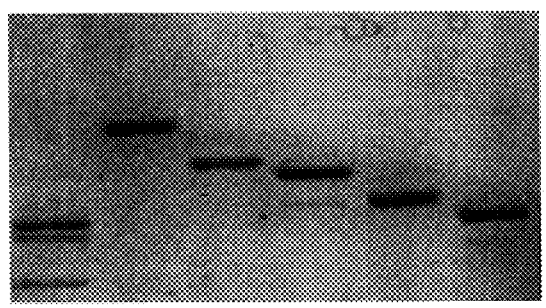
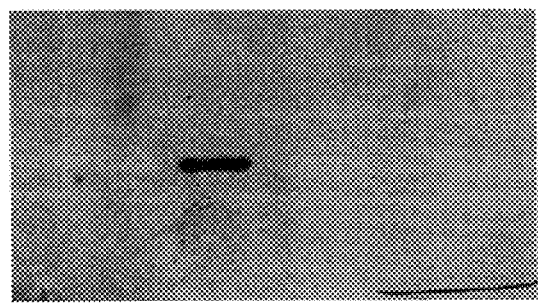
GM$_1$  GM$_3$  NGM$_3$  GM$_2$  NGM$_2$  GM$_1$
GD$_{1a}$
GT$_{1b}$
GM$_1$  GM$_3$  NGM$_3$  GM$_2$  NGM$_2$  GM$_1$
GD$_{1a}$
GT$_{1b}$

Figure 6:

| Tissue/Organ | Positive/Total |
|---|---|
| Urogenital Tract | |
| Kidney | 0/7 |
| Prostata | 0/5 |
| Ovary | 0/1 |
| Breast Gland (Secretion) | 3/4 |
| Endocrine System | |
| Adrenal Gland | 0/3 |
| Systema Immune | |
| Tonsils | 0/5 |
| Spleen | 0/3 |
| Central Nervous System | |
| Brain | |
|    Neuronas | 0/5 |
|    Glias | 0/5 |
| Cerebellum | 0/5 |
| Spinal Cord (white susbtance) | 0/3 |
| Skin | |
| Keratinocytes | 0/7 |
| Melanocytes | 0/7 |
| Respiratory Tract | |
| Bronchial Epithelium | 0/7 |
| Neumocytes | 0/7 |
| Gastrointestinal Tract | |
| Esophagus | 0/7 |
| Stomach | 0/7 |
| Small Intestine (mucus cells) | 5/5 |
| Large Intestine (mucus cells) | 7/7 |
| Pancreas | 0/7 |
| Liver | 0/7 |

Figure 7 :

| Tumor | Recognition |
|---|---|
| Breast | |
| Fibrocystic desease | 5/9* |
| Fibroadenoma | 2/2* |
| Cystosarcoma Phyllodes | 3/3 |
| Infiltrating Ductal Carcinoma | 33/33 |
| Skin | |
| Epidermoid Carcinoma | 0/9 |
| Melanoma | 20/20 |
| Lung | |
| Squamous Cell Carcinoma | 0/9 |
| Large Cell Carcinoma | 0/17 |
| Adenocarcinoma | 0/32 |
| Adenosquamous Carcinoma | 0/1 |
| Mucoepidermoid Carcinoma | 0/1 |
| Small Cell Carcinoma | 0/7 |
| Carcinoid Tumor | 0/6 |
| Central Nervous System | |
| Oligodendroglioma gr II | 0/3 |
| Oligoastrocitoma | 0/2 |
| Meningioma | 0/18 |
| Glioblastoma Múltiple | 0/1 |
| Neurilemoma | 0/4 |
| Sarcoma Meníngeo | 0/2 |
| Anaplastic Astrocytoma | 0/2 |
| Immune System | |
| B cell Lymphoma (lympho nodo) | 0/5 |
| T cell Lymphoma (lympho nodo) | 0/3 |
| Sezary's Syndrome | 0/2 |

\* Positive in extracellular secretion.

Figure 8:

| Tissue/Organ | Positive/Total |
|---|---|
| Urogenital Tract | |
| Kidney | 4/4 |
| Gonad | nd |
| Endocrine System | |
| Pancreas | nd |
| Adrenal Gland | 0/4 |
| Immune System | |
| Timo | 0/4 |
| Central Nervous System | |
| Brain | 0/4 |
| Cerebellum | 0/4 |
| Respiratory and Circulatory Tract | |
| Trachea | 0/4 |
| Heart | 0/4 |
| Lung | 0/4 |
| Gastrointestinal Tract | |
| Esophagus | nd |
| Stomach | 4/4 |
| Small Intestine | 4/4 |
| Large Intestine | 4/4 |
| Liver | 4/4 |

Figure 9:

| Cells Line | Concentration of 14F7 MAb mg/mL | % of the cell line recognized by 14F7 Mab |
|---|---|---|
| Myeloma P3X63 | 0 | 0 |
| Myeloma P3X63 | 0,01 | 71 |
| Myeloma P3X63 | 0,02 | 80 |
| Melanoma B16 | 0 | 0 |
| Melanoma B16 | 0,01 | 0 |
| Melanoma B16 | 0,02 | 0 |

Figure 10:

| Cells line | Concentration of MAb 14F7 mg/mL | % of cell viability by direct cytotoxic effect of MAb 4F7 |
|---|---|---|
| Myeloma P3X63 | 0 | 95 |
| Myeloma P3X63 | 0,05 | 50 |
| Myeloma P3X63 | 0,1 | 39 |
| Melanoma B16 | 0 | 95 |
| Melanoma B16 | 0,05 | 92 |
| Melanoma B16 | 0,1 | 90 |

MONOCLONAL ANTIBODY WHICH RECOGNIZES THE OLIGOSACCHARIDE N-GLYCOLYLATED-GALACTOSE-GLUCOSE SIALIC ACID IN MALIGNANT TUMORS, AND COMPOSITION CONTAINING IT

TECHNICAL SECTOR

The present invention is related with the field of immunology and human medicine particularly with the generation and selection of a monoclonal antibody (Mab) against the N-glycolylated-galactose-glucose sialic acid olygosaccharide sequence that can be used for the diagnosis and treatment of certain neoplasic diseases.

PRIOR ART

The olygosaccharide structures can be found forming part of glycoproteins and glycolipids. They are both present in normal and pathological tissues.

The aberrant glycosilation has been described in approximately 100% of the malignant neoplasm. Frequent changes in the aberrant glycosilation are: the expression of neoantigens, variations in the composition of the olygosaccharide sequences, increase or decrease of the sialic acid molecules in the olygosaccharides and increase in the density of the molecules in the cell surface, among others (Hakomori S. H. et al. Curr. Opin. in Immunol. 1991,(3) 646–653). In addition to the changes that can be found in the mechanism of the sialyl-tranferases, there are also variations in the activated sialic acid N-acetylated dependent hydroxilases.

Gangliosides are glycoesfingolipids that contain sialic acid in their structure and are characterized by being present in most cells of the vertebrates. These molecules are found in normal tissue and can have a higher expression in the tumors, with a different organization and conformation in the surface of malignant cells (Hakomori, S H., 1985, Cancer Res. 45: 2405–2414; Miraldi, F., 1989, Seminars in Nuclear Medicine, XIX,282–294).

The humoral immune response against carbohydrate antigens is generally of the IgM isotype. The olygosaccharide sequences bound to lipids are generally less immunogenic than the glycoproteins. Thus, the use of glycolipids as immunogen requires of its binding to transporting proteins or their incorporation to liposomes or to bacteria such as *Micobacterium tuberculosis* or R595 de *Salmonella minnesota*.

The response generated against Gangliosides is thymus independent. This has been reported repeatedly by Livingston, et al., (Livingston, P. O. et al., 1982, *Proc. Natl. Acad. Sci.* USA 84: 2911–2915; Livingston, P. O. et al. 1989, *Cancer Res.* 49: 7045–7050). The main characteristics of the antibodies generated against Gangliosides when studied in the serum of different species are their low affinity, considerable cross reactivity and short life (Livingston, P.O. 1991, *Immunology and Allergy Clinics of North America*, 11: 401–423; Portoukalian, J. et al, 1991, *Int. J. Cancer,* 49: 893–899).

The expression of the N-glycolylated form in the olygosaccharides is common in normal and pathological tissues of all the species of vertebrates, except for chickens and humans in which it is only found in fetal and tumoral tissue. The normal tissues of these two last species posses only the N-acetylated variant (Nishimakit et al. 1979, *J. Immunology,* 122: 2314; Higashi H. et al, 1985, *Cancer Res.,* 45: 3796).

The study of the olygosaccharide composition in some human tumors demonstrate the presence of the N-glycolylated form both in glycolipids and glycoproteins of melanoma tumoral cells (Hirabayashi, Y, et al. 1987, *J. Cancer Res.,* 78, 614 –620; Saida T. et al. 1991 *Arch. Dermatol. Res.* 282(3): 179–182; Kawashima I. et al. 1993, *J. Biochem* (Tokio) (2) 186–193; Kawachi S. et al., 1992, *J. Dermatol* (11): 827–830), as well as in colon tumors, especially in glycolipids (Miyoshi, I., et al, 1986, *Mol. Immunol.* 23 (6): 631; Higashi H., et al, 1985, *Cancer Research,* 45: 3796–3802). Additionally, studies have been performed to demonstrate the presence of the N-glycolylated form of the Gangliosides in tumoral samples of liver, teratoma, lymphoma, etc, (Kawai T. et al. 1991 *Cancer. Res.* (51) 1242–1246). Although in the former cases the concentration of the N-glycolylated variant of glycolipids was less than 0,05% of the total sialic acid, Marquina and collaborators found in breast tumors values of approximately 10% of the sialic acid bound to lipid (Marquina, G. et al, 1996, *Cancer Res.* 56: 5165-).

The generation of monoclonal antibodies against the N-glycolylated variant of the gangliosides has provided until now, antibodies of the IgM isotype that generally recognize more than one gangliosides molecule, for example, the human monoclonal antibodies 2–39 M and 32–27 M (Furukawa K., et al, 1988, *J. Biological Chemistry,* 263: 18507) and the murine antibodies GMR8 and GMR3 (Ozawa H. et al, 1992, *Biochem. Biophys.,* 2(294):427). Other authors have reported the generation of a specific species of anti N-glycolylated gangliosides antibodies, always of IgM isotype, among which are the monoclonal antibodies Y-2-HD1, against NGcGM$_2$ (Samai Y. et al, 1988, *Bioch Biophys. Act.,* 958, 368) and MK2-34 against the same molecule (Miyake, M. et al, 1990, *Cancer Res.* 48, 6154).

Nevertheless, Watarai (Watarai, S. et al. 1995. *J. Biochem.* 117, 1062) generated the monoclonal antibody SHS-1 against the i-active N-glycolylated gangliosides and Nakumara obtained the monoclonal antibody YK-3 against the (NGc-NGc) GD1c (Nakumara et al, 1995, *J. of Biolog. Chemist.,* 8 (270):3876). Recently Vázquez, et al., (Vázquez, A. M. et al, 1995, *Hybridoma,* 14, 6, 551) reported the generation of the monoclonal antibody P3, that recognizes most Ganglioside molecules containing the N-glycolylated form of the sialic acid, as well as the sulfated glycolipids.

Nagai et al., have generated the HMA1 monoclonal antibody against Gangliosides (Nagai Y. et al. U.S. Pat. No. 4,965,198). They obtained a specific monoclonal antibody against the Ganglioside NGcGM2 from mice bearing an autoimmune disease. Although, they reported several of these antibodies that additionally recognized other N-glycolylated Gangliosides designated as PyK, YH02, YH03, YH04, YH05, YH06 y YH07.

Moreover, Yamasaki, M. et al., in their U.S. Pat. No. 4,942,131 report the generation of the Mabs YH08, YH09, YH10 e YH11 against the 4-O-Acetyl-NGcGM3 Ganglioside, also in mice with an autoimmune disease.

Monoclonal antibodies against Gangliosides have also been obtained using these molecules as lactones or from cell lines containing Gangliosides (U.S. Pat. Nos. 5,308,614; 5,240,833; 5,389,530 y 5,500,215).

In the same manner, different monoclonal antibodies, both murine and human, have been obtained against GD3, GD2 y GM2 gangliosides, all of the N-acetylated form and most of them of the IgM and IgG3 subclasses (Pukel, C. S. et al. 1982, *J. Exp. Med.,* 115: 1133–1147; Hirabayashi, Y. et al.

1985, *J. Biol. Chem.*, 260: 13328–13333; Patent application WO 86/00909; Miyake, M. et al. 1988, *Cancer Res.*, 48: 6154–6160; Kawashima, I. et al. 1992, *Molecular Immunology*, 29, 625–632; Kotani, M. et al. 1992, *Biochimica et Biophysica Acta*, 1117: 97–103).

The passive immunotherapy with monoclonal antibodies against gangliosides has been used in clinical trials for the treatment of some tumors such as melanomas and neuroblastomas. Treatment of melanomas have been intra lesion or systemic and although results seem to be encouraging, only a reduced number of patients showed total or partial remissions (Houghton, A. N. et al, 1985, *Proc. Natl.Acad. Sci. USA*, 82: 1242; Dippold, W. G. et al, 1988, *J Cancer Clin. Oncol.*, 24: 865; Vadhan-Raj, S. et al. 1988, *J. Clin. Oncol.*, 6: 1636; Saleh M. N. et al. 1992, *Cancer Res.*, 52: 4332–4347).

These antibodies showed effect in complement or cell mediated cytotoxicity studies (Ravindramath M. H. et al. 1991, *Inter. Rev. Immunol.*, 7, 303).

Up to now, all the monoclonal antibodies obtained against N-glycolylated gangliosides are of the IgM isotype and the toxicity they provoke is mediated by complement.

IgM's generally have low antigen affinity and it is difficult to use them for diagnosis or treatment as radiolabeled Mabs. Although they fix complement well and guarantee a good cytotoxicity, the possibility of large-scale purification is much more complicated than with the IgG isotype.

Moreover, little has been reported on monoclonal antibodies against N-glycolylated glycoproteins, and most of them for diagnostic purposes.

Devine et al., described the 3E1.2 monoclonal antibody which recognizes an N-glycolylated mucin (glycoproteic) expressed in 90% of breast tumors studied by immunohistochemistry (Devine, P. L., et al. 1991, *Cancer Res.* 51(21): 5826–36).

It has also been published a monoclonal antibody designated JAM3, that recognizes the N-acetylated and N-glycolylated forms of a 250 kD protein present on the surface of the cysts produced by the attack of Entamoeba (Avron, B., et al. 1987, *Mol Biochem Parasitol.* (3): 257–266).

DISCLOSURE OF THE INVENTION

The novelty of the present invention consists in having obtained a monoclonal antibody highly specific for the N-glycolylated-galactose-glucose sialic acid olygosaccharide sequence, present in both, gangliosides and glycoproteins. Additionally the characteristic of being an IgG isotype immunoglobulin makes it more specific and thus of higher affinity for the molecules it recognizes, favoring its biological activity. Unexpectedly this antibody showed the capacity to provoke cellular death directly in the cells bearing said olygosaccharide sequence.

DETAILED DESCRIPTION OF THE INVENTION

Obtention of the NGcGM3 Ganglioside

For obtaining the NGcGM3 ganglioside a modification of Hakomori's technique is used. (Hakomori, S. et al. 1974, *Methods in Enzymology*, 32:, Part B, 350), using natural sources such as horse erythrocytes. The yield of NGcGM3 Ganglioside extraction was between 180 and 300 mg per liter of horse erythrocytes with a purity above 90% corroborated by high efficiency liquid chromatography according to, Gazzotti's method (Gazzotti, G. et al. 1985, *J. of Chromatography*, 348: 371–378).

Obtention of the Immunogen

To obtain the immunogen the NGcGM3 Ganglioside is hydrophobically bound to the human lipoproteins of very low density (VLDL) obtained according to Dumontet et al., (Dumontet, C. et al. 1994. *Cancer Immunol Immunother.* 38: 311–318.

Immunization Scheme

To obtain anti ganglioside IgG Mabs the following immunization method is used. Mice or other mammalian species were immunized with vaccine preparations containing between 0.03 and 0.5 mg of the NGcGM3 Ganglioside bound to VLDL per dose and an adjuvant selected from one of the following: albumin, complete or incomplete Freund's adjuvant or Montanide ISA 51.

Before and after the immunization period, blood samples are taken from the animals to obtain serum for monitoring the antibodies generated in the animals against the Ganglioside used as antigen. Any of the known immunoassay methods for detecting the antigen-antibody (Ag-Ab) reaction is used for this purpose.

The animals are immunized with various doses, between 2 and 8 at time intervals varying between 7 and 14 days. The administration is performed by subcutaneous or intramuscular route with volumes between 0.1 and 0.2 mL. Other possible immunization routes are intravenous and intraperitoneal. The animals receiving this dose range show a specific response against the Ganglioside used as immunogen. Between 70 and 100% of the immunized animals had a specific IgG response to the NGcGM3 ganglioside.

Achievement of the Monoclonal Antibodies

For the production of specific Mabs against the NGcGM3 ganglioside the mice with antibody titers in serum against this ganglioside received a new immunization with the vaccine preparation 3 days before the antibody producing cells are obtained. Spleen cells should be preferred although other cells can also be used.

These cells are fused with myeloma cells, which provide the hybrid cells or hybridomas with the capacity to expand indefinitely "in vivo" and "in vitro". For this purpose any of the known cell fusion methods can be used. To determine the antibodies produced by the hybridomas an immunoenzymatic assay is preferentially used. Other immunoassay methods can also be used. The procedure of this assay is the recognition by hybridoma supernatans of the gangliosides, and the antigen-antibody reaction can be visualized using a second antibody labeled with an enzyme which binds to the antibody produced by the hybridoma under adequate conditions and is at the same time detected.

The hybridoma once selected is cloned at least 2 times (for example, by limiting dilution). The Mab obtained can be produced "in vitro" in an adequate culture media, such as any of the ones described in the state of the art and afterwards purified from said tissue culture supernatant. In this case, between 1 and 8% of the secreting clones were specific against the N-glycolyl Gm3 Ganglioside.

Another antibodies production method, consists in the injection of the hybridoma in animals (for example, syngenic animals). The hybridoma provokes the formation of non-solid tumors that provide a large concentration of the desired antibody in the blood stream and in the peritoneal exudate of the host animal.

Purification of the Monoclonal Antibody

The purification of the monoclonal antibodies is performed from the ascitic fluid obtained by the inoculation of $0.2 \times 10^6$ cells of the monoclonal antibody producing hybridoma in the peritoneal cavity of Balb/C mice, previously treated with incomplete Freund adjuvant as ascitogenic agent.

The ascitic fluid is diluted to one half in glycine buffer 1.5 M, NaCl, 3M, pH 8.9 and applied to a protein A-Sepharose matrix at a flow rate of 60 mL/h. The Mab elution is performed using citrate buffer 0.14 M, pH 6.

The concentration of the purified Mabs is estimated by the Lowry method (Lowry, G. H., 1951, *J. Biol. Chem.*, 193: 256) and using the absorption coefficient of the murine IgGl at 280 nm. The specificity is confirmed by ELISA.

Between 2 and 5 mg of antibody per mL of ascitis were obtained, with purity per cent above 95%. This was corroborated by low-pressure liquid chromatography.

Specificity Studies

To determine the specificity of the monoclonal antibodies obtained, immunoenzymatic studies of the Mabs produced are performed in ELISA plates and in thin layer chromatography using the N-acetylated (GM1, GM2, GM3, GM1, GD1a, GD1b, GD3 and GT1b) and N-glycolylated (GM3, GM2, GM1a, GM1b, GD1c y GD3) Gangliosides.

To run the glycolipids in the high-resolution thin layer chromatography the solvent system is used (Chloroform:Methanol:KCl 0.25% and 2.5 M $NH_3$) (5:4:1) (v:v). Chemical developing with Orcinol performs the visualization of the bands.

The plates are plastic coated with a poliisobutilmethacrilate solution and are air dried at room temperature over night. Blocking is performed during approximately 30 minutes with a 1% bovine serum albumin solution dissolved in saline phosphate buffer (PBS), pH 74. Afterwards, the monoclonal antibodies are incubated in the blocking solution.

Next the plates are washed with PBS and the peroxidase conjugated anti mouse immunoglobulin is added during one hour. Plates are again washed and the enzyme substrate solution is added until the bands are visualized. Finally the chemical and immunological development are compared. As a result the IgG recognized only the NGcGM3 ganglioside.

Cytotoxicity Determination

To determine if the antibodies generated produce cell death directly or by some of the other cytotoxic forms, $10^7$ cell/mL of the P3X63 murine myeloma containing NGcGM3 is incubated at 4° C. and 37° C. respectively with the monoclonal antibody between 0.01 and 1 mg/mL during 30 minutes. Then the Tripan blue method is used for performing the viability studies. The number of dead cells as consequence of the antibody effect can be counted using propidium iodine or any other viability marker.

To study the complement mediated cytotoxicity $10^7$ cells per mL were used; monoclonal antibodies are added at concentrations between 0.01 and 0.5 mg/mL. Rabbit serum that has high concentrations of the complement proteins, is added at dilutions from ¹/₂₀ to ½ and incubated during 1 hour at 37° C. Complement mediated cytotoxicity was determined by viability counts as described above or using the $Cr^{51}$ liberation method in which the P3X63 radiolabeled myeloma cells, liberate to the culture supernatant the isotope when they die.

The direct cytotoxicity was measured using different methods that showed values between 50 and 85% of dead cells with respect to the total number of cells studied.

Monoclonal Antibody Biodistribution Determination

The Mabs generated can be used both for diagnosis and treatment, labeled with a radioisotope such as 99mTc, Re186 and Re188. Schwarz and Steinstrasser (Schwarz A., and Steinstrasser, A. 1987, *J. Nucl Med.* 28: 721) have described the method of labeling monoclonal antibodies with radioisotopes which was modified by Mather y Ellison (Mather S. J. and Ellison D., 1990, *J. Nucl. Med.* 31: 692–697). Labeling quality control is performed by chromatography in Whatman 3MM paper. The per cent of labeling obtained was 98 and 100%.

To determine the possible use of the Mab, 10 mice were inoculated with the P3X63 tumor and another 10 mice were used as normal controls (no tumor was inoculated). The time needed for tumor to grow was waited and then the 99mTc-labeled 14F7 Mab was injected by intravenous route to the 20 mice.

Monitoring of the biodistribution of the anti- olygosaccharide sequence Mab is performed in groups of 5 animals (5 healthy and 5 with tumor) 4 and 24 hours post injection. The animals are sacrificed and the main organs and tumor are weighed and the gamma emission quantified separately at the end of the study.

The monoclonal antibodies distributed in the healthy animals mainly in the blood, liver and kidney while in the animals with tumor the Mab was localized in the former organs and preferentially in the tumor at 24 hours.

Mab's Recognition of Normal and Fetal Tissues

Radiolabeled Mabs, as described in the state of the art, can be used to detect tumors where the olygosaccharide sequence is expressed.

Whole body radioactivity can be studied with a Gamma Camera. Images acquisition is performed at 5 minutes and 1, 3, 5, 24 and 48 hours after Mab injection. Mab is localized only in the tumor and in the excretion organs.

Mabs can also be bound directly or indirectly to other therapeutic agents such as drugs, radioisotopes, immunomodulators, lectins and toxins. Among the biological response modifiers (immunomodulators) that in some way can increase the destruction of the tumor by the Mab of this invention are included lymphokines such as: Tumor Necrosis Factor, Macrophage Activator Factor, Colony Stimulating Factor, Interferons, etc.

Immunohistochemical studies were performed for diagnostic purposes. Tissue sections were fixed in 10% buffered formaline solution and dehydrated, clarified and embedded in paraffin. Histopathology was studied in Hematoxilin-Eosin stained tissue sections.

Serial sections from the paraffin blocks used for the histopathological study were immunostained by the biotin streptavidin peroxidase complex method, previously described (Hsu, S. M. y Raine, L., 1981,. *J. Histochem Cytochem.* 29: 1349–1353).

The deparaffinized and dehydrated sections were treated with 3% hydrogen peroxide methanol solution during 30 minutes to eliminate endogenous peroxidase activity. Tissue sections were incubated with the purified Mabs. Followed by biotinilated anti mouse antibodies and streptavidin peroxidase complex (Dakopatts) at room temperature.

Between incubations sections were washed with Tris-HCl saline buffered solution. The peroxidase reaction was developed with 30% $H_2O_2$ and 3-3 diaminobencidine.

Slides were washed with tap water, stained with Mayer's Hematoxilin, mounted with balsam and coverslipped. The reaction with the enzyme produces a brown-red color.

Human breast, lung, skin and nervous system tumoral tissues were studied as well as, fetal and normal adult tissues.

Fresh biopsies of pathological tissues were obtained during the first hour after surgery. The biopsy fragments were frozen, later sectioned and the slides stored frozen until the study was performed.

The use of fetal tissues for the study is due to the fact that the association of Gangliosides with oncofetal antigens has been repeatedly reported as well as the similarity of these molecules in fetal and tumoral human (Cahan, L. et al. 1982 Proc. Natl. Acad. Sci. USA., 79:7629–7633).

The fetal tissue sections were obtained from fetus between 12 and 18 weeks old.

Adult normal tissue fragments were obtained from individuals deceased in accidents and/or encephalic death during the first hour after exitus letalis.

Among the tumors studied, lung and central nervous system tumors of different ethiology resulted negative as well as the sections of normal human tissues. While melanoma and breast tumor tissue sections were all positive as well as the fetal tissue sections of the digestive system (liver, stomach, small and large intestine) and the renal system.

Antitumoral Effect

To demonstrate the anti tumoral effect of the monoclonal antibodies against the NGcGM3 Gangliosides, animals inoculated with the tumor bearing the target Ganglioside (P3X63 myeloma) was treated with the antibodies obtained. The dose can vary from 0.01 mg/kg of weight to 200 mg/kg of weight in one or more daily administrations during one or various days. The antibodies can be administered by parentheral injection (intravenous, intraperitoneal, intramuscular, subcutaneus, intracavity or transdermic).

In a typical experiment the mice treated with the antibody have a survival rate between 30 and 80% compared to with the mice of the control group, corroborated by the Log Ram test (Cox and Oakes (1984) Analysis of survival Data edits. Chapman Hall). Significant differences (<0.05%) were found between the group treated with the Mab and the control group.

EXAMPLES

Example 1

Specific IgG Response to NGcGM3, of the Mice Immunized with the Vaccine Preparation NGcGm3/VLDL/Adyuvant Freund Complex, Measured by an Immunoenzymatic Technique Female Balb/C mice between 6–8 weeks old were injected by intramuscular route with 0.2 mg of the vaccine preparation human NGcGM3/VLDL, with the complete Freund adjuvant in the first dose and incomplete Freund adjuvant in the following doses (produced by SIGMA) mixed in equal volumes. Each animal received 6 dose. The first 4 dose weekly and the 2 remaining dose every 14 days. Blood extractions were performed previous to the first dose and every 2 weeks.

The antibody levels were measured in the serum of the animals using an indirect ELISA in Polysorp plates (Nunc trade mark), on which the Gangliosides were immobilized following the method described below:

Gangliosides NAcGM3 and NGcGM3 were dissolved separately in methanol (4 $\mu$g/ml) and 50 $\mu$l/well were added. The plate was placed at 37° C. during one hour and a half to evaporate the methanol. Afterwards, 100 ml/well of TRIS-HCl 0.05 M, pH 7.8 buffer, containing 2% bovine serum albumin (BSA) was added and incubated during one hour at room temperature. Next, 50 $\mu$l of the serum were diluted in the same buffer and incubated over nigh at room temperature.

The wells were washed 4 times with 200 $\mu$l phosphate saline buffer solution (PBS) and 50 $\mu$l of a biotin conjugated anti mouse immunoglobulins antiserum was added at an adequate dilution during one and a half hour 37° C.

After washing again with PBS, 50 $\mu$l of an adequate dilution of alkaline phosphatase streptavidin was added. Finally the last washing was performed and 100 $\mu$l p-nitrophenylphosphate substrate was dissolved in dietanolamine buffer, pH 9.8 (1 mg/ml). Absorbance was measured in an ELISA reader at 405 nm.

FIG. 1 shows the results of O.D. at 405 nm of each animal's serum diluted 1/80 on the day 56 of the experiment. The response against NGcGM3 and GM3 was determined by ELISA using a biotinilated mouse anti IgG conjugate and alkaline phosphatase streptavidin from Jackson.

More than 70% of the animals immunized with the vaccine preparation had values at O.D. 405 nm over 0.5 against NGcGM3. All the immunized animals showed IgG response against NGcGM3, with no response observed to NAcGM3, in spite of the minimal difference between these two molecules.

FIG. 2 shows the sustained specific response of the antibodies (IgG isotype) against the NGcGM3 Ganglioside, three months after receiving the last immunization dose, with no response shown against NAcGM3.

Example 2

Achievement of Monoclonal Antibodies Against NGcGM3

The antibodies were generated by immunizing Balb/C mice using the procedure described in Example 1.

Three days before the fusion, the animals were re-immunized with the immunogen NGcGM3/VLDL, using Freund complete adjuvant. Afterwards mice spleen were obtained and a cell suspension prepared by passing the tissue through a stainless steel sieve or by spleen perfusion. Cell fusion was performed as described by Köhler y Milstein (Nature, 1975, No. 256, 495–497) with some modifications.

The cells of the non secreting P3/X63 Ag8 6.5.3, murine myeloma were fused with the murine splenocytes in a proportion 1:10, in 0.5 mL of fusion media containing 42% of poliethilenglycol (3000–3600 Sigma)in RPMI 1640 media.

The cells were cultured in HAT (hipoxantine/aminopterine/tymidine) selective media at 37° C., with a humid atmosphere of 5% $CO_2$, after cell fusion.

Between 10 and 15 days after the cell fusion was performed the assay for detecting the presence of antibodies in the supernatant of the hybridoma cell cultures was started using the ELISA technique of example 1.

Culture hybridoma cells that reacted with the ganglioside of interest were selected and cloned twice by the limiting dilution method in the presence of conditioning cells.

The specificity of the antibodies produced by the selected hybridomas was determined using the indirect ELISA technique with a battery of glycolipids.

The number of specific clones against the NGcGm3 Ganglioside was 5.5%. One of the clones obtained was denominated 14F7.

Example 3

Determination of the Subclass of the 14F7 Monoclonal Antibody

To determine the immunoglobulin subclass of the monoclonal antibody of this invention an indirect ELISA on plates coated with NGcGm3 was used as described in example 1, but substituting the serum for dilutions of the supernatant of the hybridoma or of the purified Mab.

Biotin conjugated Anti IgG1, IgG2a, IgG2b e IgG3 murine Mabs produced in rats (Pharmingen), diluted in incubation buffer were added. After one hour incubation at 37° C. the plates were washed and alkaline phosphatase conjugated streptavidin diluted in the incubation buffer was added. As controls of each subclass murine Mabs previously characterized were used.

Finally the substrate solution was added. Reading of the absorbance was performed as described before. FIG. 3 shows that the 14F7 Mab belongs to the IgG1 subclass.

Example 4

Specificity Study of the 14F7 Monoclonal Antibody Using Immunostaining on High Resolution Thin Layer Chromatography The high-resolution thin layer chromatography was used to separate the glycolipids. The solvent system sued was Chloroform:Methanol:KCL 0.25% and 2.5 M of NH3 (5:4:1) v:v. The bands were visualized by chemical development with Orcinol (Svennerholm L. 1964, J. Lipid. Res., 5, 145). While for the immunostaining the method Kawashima Y. y col. 1993 (J. Biochem, 114, 186) was used.

The plates where the thin layer chromatographies were previously performed were plastic coated by immersion during 75 seconds in a solution of 0.1% poliisobutilmethacrilate (PIBM) in N-hexane. The plates are then dried at room temperature during 30 minutes. 1% PIBM solution is the applied on the borders of the plates keeping them over night at room temperature.

Blocking of unspecific interactions was performed by applying for 30 minutes a solution of 1% bovine serum albumin dissolved in PBS pH between 7.2 and 7.4. Immediately after plates were incubated with the 14F7 Mab at a concentration between 0.01 y 0.02 mg/ml in blocking solution.

Plates were washed PBS and incubated with horseradish peroxidase conjugated rabbit anti mouse immunoglobulins antiserum diluted in the blocking buffer.

After one hour incubation stirring at room temperature the plates were washed again and the substrate solution consisting of 0,4 mg/mL of ortophenylendiamine (C6H8N2) Sigma in citrate-phosphate 80 mM pH 5 buffer with 0,12% Hydrogen Peroxide (H2O2) (Riedel de Haen) was added. The reaction was stopped with repeated washes with phosphate buffer.

The reaction showed specificity only for the NGcGm3 Ganglioside and no reaction was observed for the other N-glycolylated gangliosides evaluated as GM1a, GM1b, GM2 and N-Acetylated (FIGS. 4 and 5).

Example 5

Recognition of Tumoral and Fetal Tissues by 14F7 Monoclonal Antibody

Tissue sections were fixed in 10% buffered formaline solution and dehydrated, clarified and embedded in paraffin. Histopathology was studied in Hematoxilin-Eosin stained tissue sections.

Serial sections from the paraffin blocks used for the histopathological study were immunostained by the biotin streptavidin peroxidase complex method, previously described (Hsu, S. M. y Raine, L., 1981,. *J. Histochem Cytochem.* 29: 1349–1353).

The deparaffinized and dehydrated sections were treated with 3% hydrogen peroxide methanol solution during 30 minutes to eliminate endogenous peroxidase activity. Tissue sections were incubated with the purified 14F7 Mab during one hour at room temperature. Followed by biotinilated anti mouse antibodies and streptavidin peroxidase complex (Dakopatts) at room temperature.

Between incubations sections were washed with Tris-HCl saline buffered solution. The peroxidase reaction was developed with 5 mL of a Tris buffered solution. 0.005 mL of 30% $H_2O_2$ and 3 mg of 3—3 diaminobencidine.

Slides were washed with tap water, stained with Mayer's Hematoxilin, mounted with balsam and coverslipped. The reaction with the enzyme produces a brown-red color.

Adult normal tissue fragments were obtained from individuals deceased in accidents and/or encephalic death during the first hour after "exitus letalis". Fresh biopsies of pathological tissues were obtained during the first hour after surgery. The fetal tissue sections were obtained from fetus between 12 and 18 weeks old during the first hour after induced abortion. All the biopsy fragments were washed in saline solution and immediately frozen in liquid nitrogen and stored frozen at −80° C.

Serial sections of 5 μm were obtained from the frozen fragments in a Leica cryostat at −25° C. Sections were air dried and used immediately or stored at −20° C. wrapped in aluminum foil. In an case slides were fixed at the moment of use in 4% paraformaldehyde during 20 minutes.

FIG. 6 shows the immunohistochemical study of the 14F7 Mab in normal human tissues. Reactivity of the Mab in the membrane and in the cytoplasmic region of the tissues is not observed.

FIG. 7 shows the same study for pathological tissues. All breast (33/33) and melanoma (20/20) tissues studied resulted positive. While, 70 lung tumors of different etiology resulted negative as well as 33 different tumors of the central nervous system.

FIG. 8 shows the recognition of 14F7 Mab of the digestive system and renal fetal tissues.

Example 6

Recognition of the Ganglioside NGcGm3 by the 14F7 Mab in Cell Lines Studied by Flow Cytometry The cell lines studied were the murine myeloma P3X63 expressing the Gm3 and NGcGm3 described by J. Muthing et al (Muthing,J. et al.,1994, J. Biochem 116: 64–73) and the B16 myeloma that expresses Gm3. The cells were cultured in RPMI media with 8% bovine fetal serum. Cells were adjusted to a concentration of $10^7$ cells/mL of a saline phosphate solution pH 7,4 containing 0.02% sodium azide and 1% bovine serum albumin. In each tube 0,1 mL of the cell suspension was added followed by 0.05 mL of the 14F7 Mab solution dissolved in saline phosphate buffer to obtain a final concentration of 0,1 mg/mL and incubated during 30 minutes at 4° C. The cells were then washed with the solution in which they were dissolved.

Next the cell cultures were centrifuged during 5 minutes at low speed to precipitate the cells. Then the anti mouse (IgG+IgM) biotin conjugate (Jackson) was added and washed after 30 minutes incubation at 4° C. Finally 0.002 mg of the fluorescein streptavidin (FITC) (Jackson) were added and incubated in the same conditions as before. The last washed was then performed this time with saline phosphate buffer.

Supernatant was eliminated after the last centrifugation and the cells were resuspended in 0,6 mL of the last washing solution.

An 80% of the cells of the P3X63 myeloma cell were stained positive with the 14F7 monoclonal antibody (FIG. 9).

Example 7

Direct Cytotoxity Study of the 14F7 Monoclonal Antibody

The P3X63 murine myeloma cell line was incubated with the 14F7 Mab as described in Example 6. washing, 0,01 mL of a propidium iodine solution in saline phosphate buffer was added to the cells to determine the cell viability using flow cytometry.

Results showed that 78% of the cells died (FIG. 10).

Example 8

Biodistribution Study of the 99mTcs Labeled 14F7 Monoclonal Antibody in Balb/c Mice, Healthy and Bearing P3X63 Myeloma Tumors Twenty female Balb/C mice weighing between 20 and 22 g (10 healthy and 10 with P3X63 Myeloma tumor inoculated by intraperitoneal route) received an intravenous injection of the 99mTc labeled 14F7 Mab. The label concentration relation was 0,03 mg of the 14F7 Mab/60 $\mu$Ci of 99mTc.

The results of radioactivity quantification in the different organs were performed in 5 animals of each group, at 4 and 24 hours after the injection. The animals were sacrificed and the weight of each organ measured in a Sartorius scale. The radioactivity of all the tubes at once was determined approximately 25 hours after starting the experiment, in a WALLAC gamma counter (model WIZARD 1470).

The labeling method was previously described by Schwarz and Steinstrasser (1987) and modified by Muther and Ellison in 1990.

The 14F7 labeled Mab was eliminated in the healthy mice by the kidney and liver (FIG. 11).

In mice bearing the P3X63 Myeloma tumor binding of the 14F7 Mab was shown at 4 hours (12% of the total injected radioactivity per gram of tissue) and at 24 hours (35% of the total injected radioactivity per gram of tissue). Mab elimination was mainly by the kidneys (FIG. 12).

Example 9

Antitumoral Effect of the 14F7 Monoclonal Antibody in BALB/C Mice Bearing the P3X63 Ascitic Myeloma Balb/C female mice weighing 20–22 g, were injected by intravenous route with 6 doses of the 14F7 monoclonal antibody (one group with 0,1 and a second group with 0,2 mg) every 2 days, in saline phosphate buffer solution. Three days before the experiment, the peritoneal cavity was irritated with incomplete Freund adjuvant to favor the moment in which the tumor becomes measurable. The amount of 10 000 cells of the murine P3X63 Myeloma, were inoculated on day 0 of the experiment by the intraperitoneal route, at the same time as the passive therapy with the 14F7 monoclonal antibody began, although it was inoculated by intravenous route. While the control of good prognosis (best treatment) used for comparison was a third group treated by intravenous route with Cyclophosphamide (Shangai Hua Lian Pharmaceutical Corp.) at a dose of 20 mg/kg of corporal weight, consisting of a weekly dose during all the experiment. The intravenous treatment with saline phosphate buffer solution, pH 7,4 was used as a control of the experiment.

FIG. 13 shows the survival results in the 4 groups previously described. In the groups treated with 14F7 (0,1 and 0,2 mg) and with 20 mg/kg of weight of Cyclophosphamide no measurable tumor was observed in some animals.

The survival results favored the groups treated with the 14F7 Mab. On day 30 of the experiment, while no animal of the control group was alive, 6 animals were still alive, both of the first group (0,1 mg of the Mab) as of the group treated with Cyclophosphamide and 7 animals of the second group (0,2 mg of the Mab). At 60 days of treatment, 2 animals of the first group and 2 animals of the group treated with Cyclophosphamide survived, while from the second group 5 animals were still alive.

Example 10

Inhibition of the Tumoral Growth of the Solid P3X63 Myeloma in Athymic Mice

Ten athymic female mice, from the out bread NMRI, with a weight between 20 and 22 grams were inoculated by subcutaneous route with $10^6$ cells of the P3X63 murine Myeloma tumoral line on day 0 of the experiment. The animals were divided in two groups of 5.

One group started treatment by intraperitoneal route with the purified 14F7 Mab, 0.15 mg per dose 6 doses) every 2 days. While the other group acted as control and received by the same route and the same number and dose frequency of equal volume of saline phosphate buffer.

FIG. 14 shows the inhibition of the growth of the tumors in the mice treated with the 14F7 Mab, with respect to the control group. Significant differences were observed between the two groups.

A viable culture producing the monoclonal antibody 14F7 was deposited in accordance with the Budapest Treaty with the European Collection of Cell Cultures, Centre for Applied Microbiology and Research, Salisbury, Wiltshire, SP4 OJG, United Kingdom, on Oct. 19, 1998. The accession number is for this deposit is 98101901. All restrictions and conditions by the depositors/applicants upon availability of the cell culture to the public will be irrevocably removed upon granting of a patent based on the this disclosure. The cell culture will be replaced in kind if, at any time during the required term oi deposit, viable samples cannot be dispensed therefrom.

BRIEF DESCRIPTION OF THE DRAWINGS

FIG. 4: Recognition by immunostaining using thin layer chromatography of the N-glycolylated and N-acetylated gangliosides that were used during the study of the specificity of the 14F7 monoclonal antibody FIG. 5: Recognition of the NGcGm3 Ganglioside by the 14F7 monoclonal antibody by immunostaining on thin layer chromatography.

FIG. 6: Non recognition of adult normal tissues by the 14F7 monoclonal antibody in immunohistochemical studies.

FIG. 7: Immunohistochemical recognition of some human malignant and benign tumors by the 14F7 monoclonal antibody.

FIG. 8: Immunohistochemical recognition of normal human fetal tissue by the 14F7 monoclonal antibody.

FIG. 9: Recognition of P3X63 Myeloma cell line expressing the NGcGm3 Ganglioside by the 14F7 Mab using Flow Cytometry.

FIG. 10: Complement independent cytotoxic effect of the 14F7 Mab using the P3X63 Myeloma cell line by the propidium iodine technique with flow cytometry.

Figure 1:
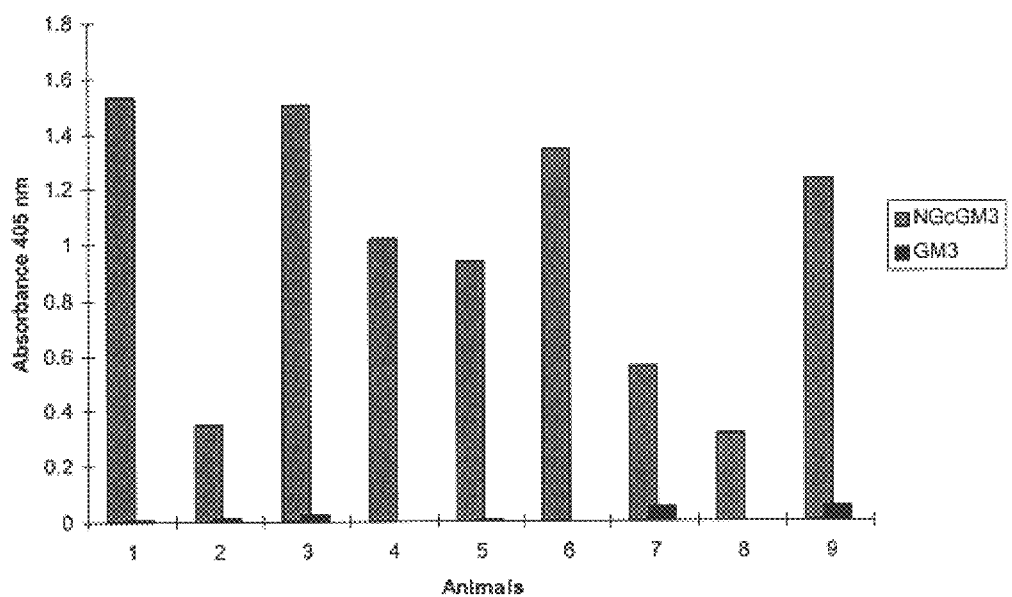
FIG. 1: Shows the levels of serum antibodies obtained against NGcGm3 and not against the Gm3 on day 56 of the experiment, in mice immunized with the NGcGm3/VLDL/Complete Freund adjuvant vaccine preparation.
Figure 2:
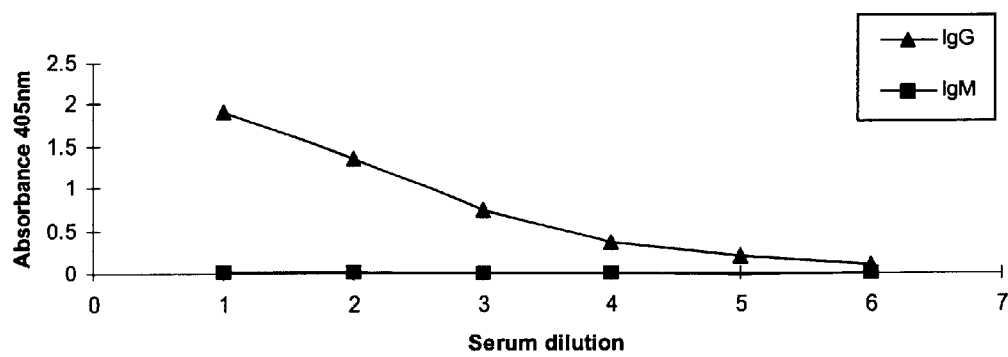
FIG. 2: Determination by ELISA of the isotype of the antibody response against the NGcGm3 Ganglioside in the serum of the mice 3 months after receiving the fourth dose of 0,2 mg of NGcGm3/VLDL/Complete Freund.
Figure 3:
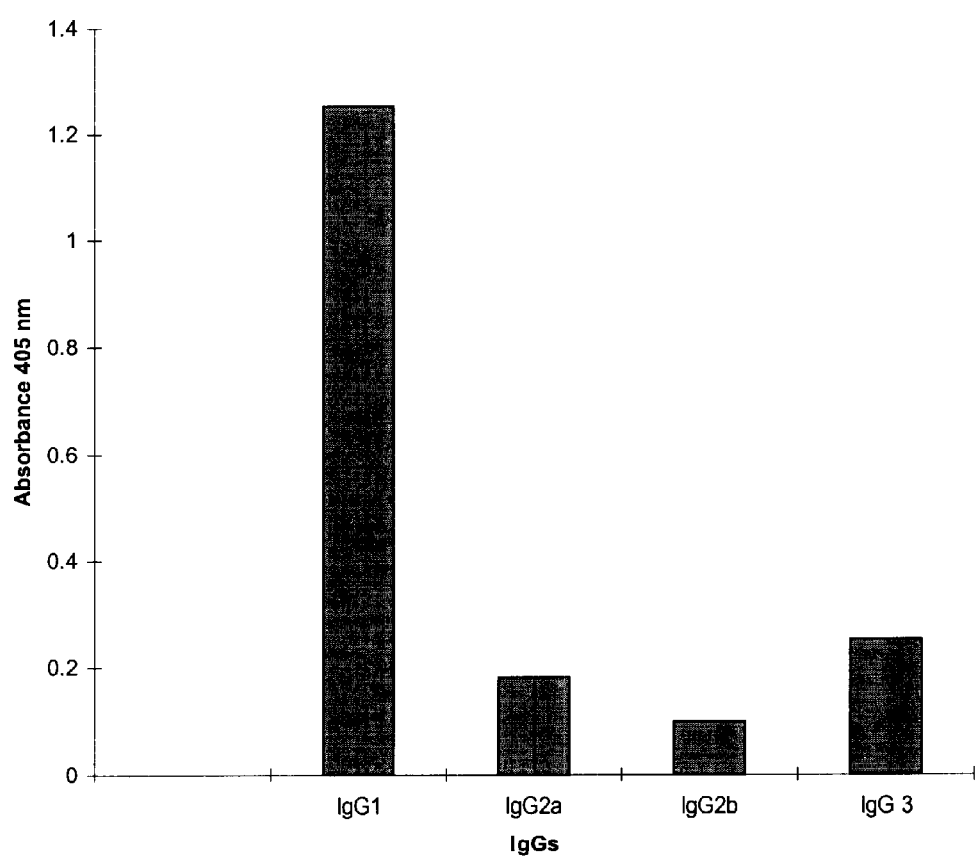
FIG. 3: Determination by ELISA of the 14F7 monoclonal antibody immunoglobulin subclass (IgG)
Figure 11:
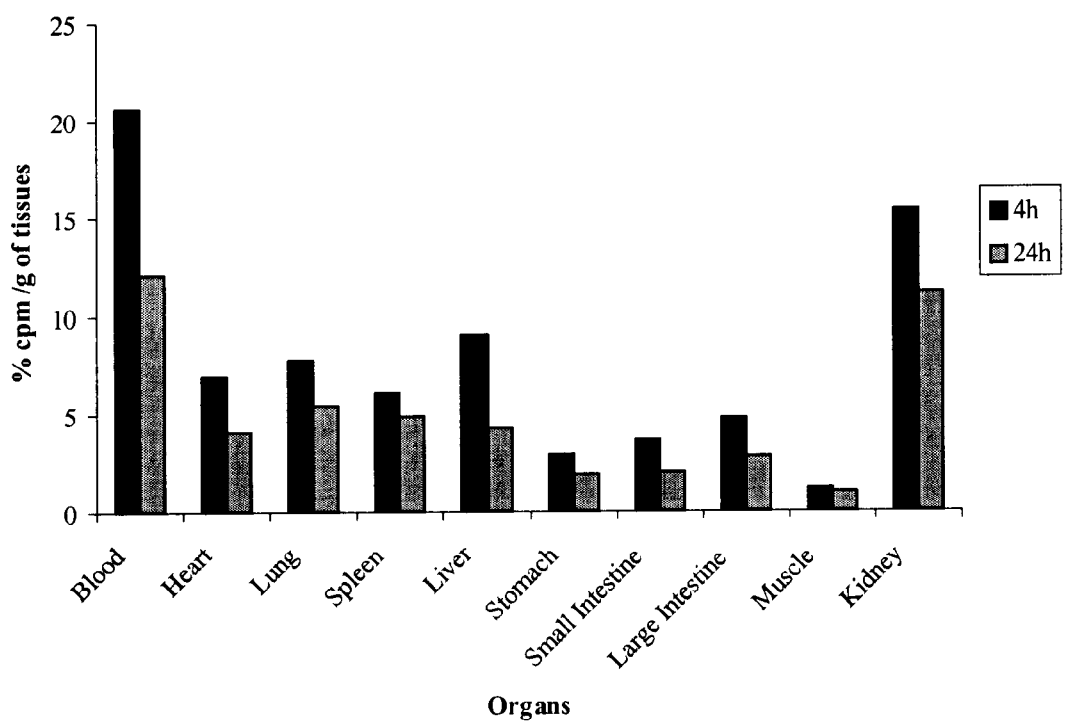
FIG. 11: Biodistribution of the 99mTc-labeled 14F7 monoclonal antibody. Results of the per cent of gamma radiation with respect to the weight in grams of the organ studied in normal Balb/c mice.
Figure 12:
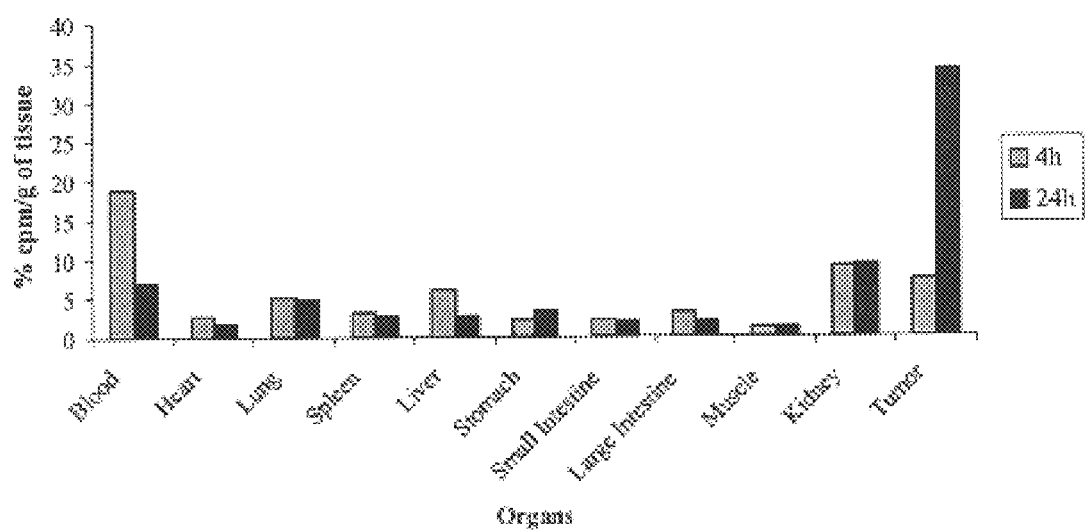
FIG. 12: Biodistribution of the 99mTc-labeled 14F7 monoclonal antibody. Results of the per cent of gamma radiation with respect to the weight in grams of the organ studied in Balb/c mice bearing the P3X63 Myeloma tumor.
Figure 13:
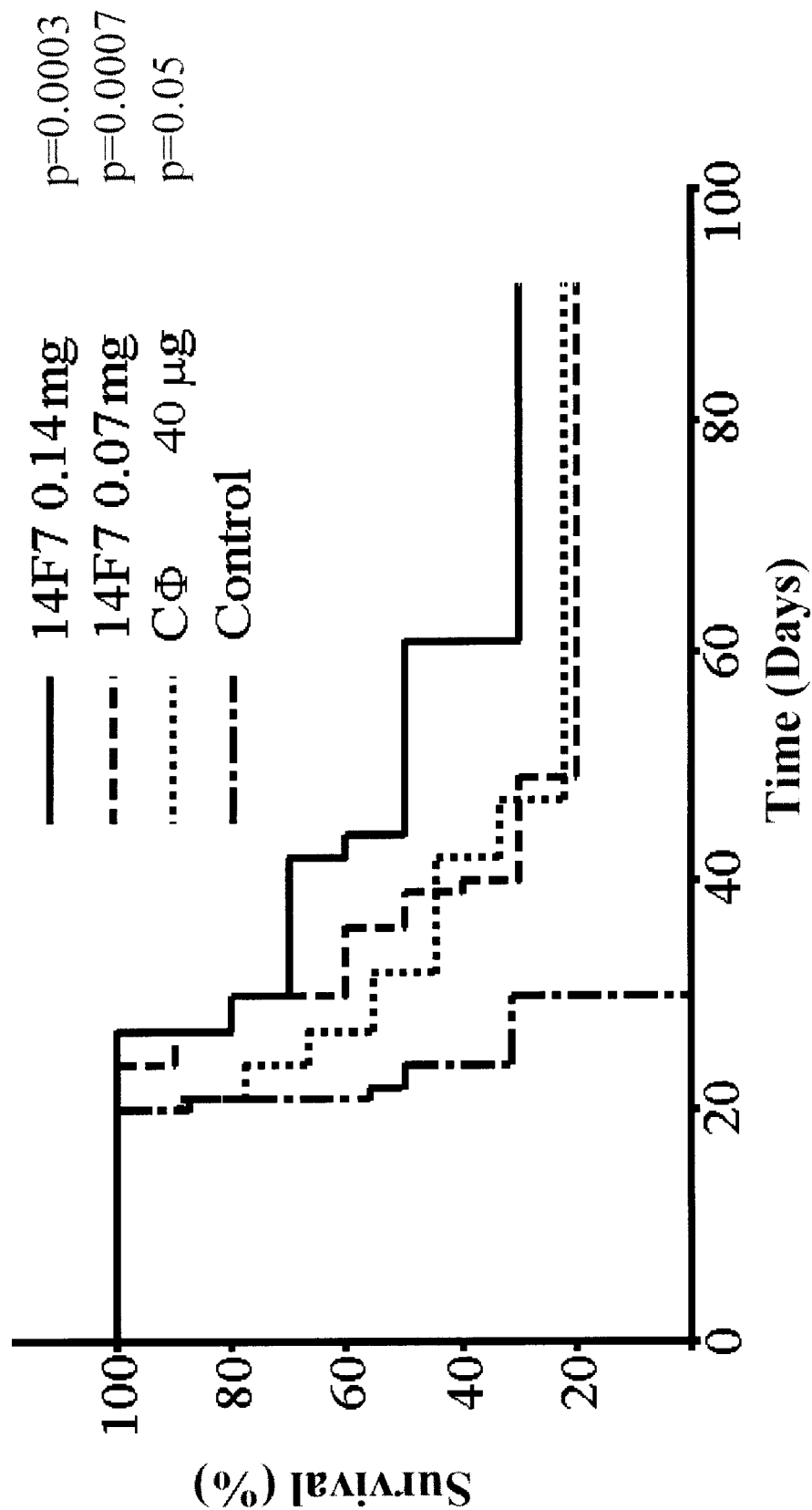
FIG. 13: Anti tumoral effect of the passive therapy of the 14F7 monoclonal antibody in groups of Balb/c mice inoculated with the P3X63 murine ascitic Myeloma tumor, treated with 0,1 y 0,2 mg of said antibody, compared with a control group treated with Cyclophosphamide 20 mg/kg and a control group with PBS.
Figure 14:
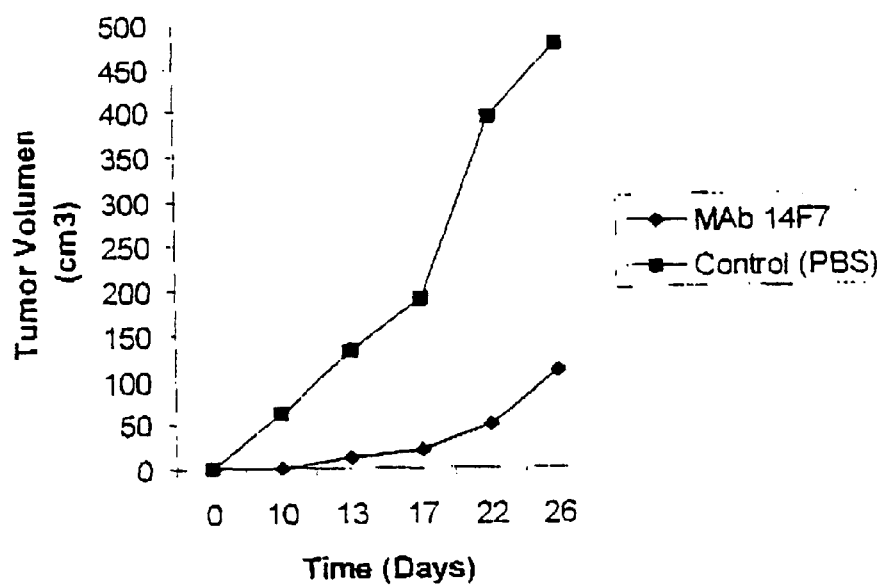
FIG. 14: Tumoral growth inhibition "in vivo"of the murine P3X63 solid Myeloma tumor in athymic mice of the out bread NMRI.

What is claimed is:

1. A monoclonal antibody against NGcGm3 gangilioside having binding specificity to the N-glycolylated-galactose-glucose sialic acid oligosaccharide sequence of said NGcGm3 ganglioside, said monoclonal antibody being of the IgG1 subclass and having cytotoxic activity against tumoral cells bearing said NGcGM3 ganglioside.

2. The monoclonal antibody according to claim 1, wherein said cytotoxic activity is complement mediated.

3. A monoclonal antibody obtained from the hybridoma 14F7, ECACC 98101901.

4. The hybridoma 14F7, ECACC 98101901.

5. A pharmaceutical composition comprising an amount of the monoclonal antibody of claim 1 or 3 and a suitable excipient.

6. The pharmaceutical composition according to claim 5, wherein said antibody is bound to a therapeutic agent.

7. The pharmaceutical composition according to claim 5, wherein the pharmaceutical composition is adapted for use in the treatment of cancer.

8. A reagent comprising the monoclonal antibody according to claim 1 or 3 bound to a marker.

9. The reagent according to claim 8, wherein the reagent is adapted for use in detecting at least one type of cancer.

10. The reagent according to claim 9, wherein the cancer is selected from the group consisting of: melanomas, breast cancer, renal cancer, and cancer in the digestive system, and combinations thereof.

11. The pharmaceutical composition according to claim 6 wherein said therapeutic agent is selected from the group consisting of: drugs, radioisotopes, immunomodulators, lectins, toxins, and combinations thereof.

12. The pharmaceutical composition according to claim 7, wherein the cancer is selected from the group consisting of: breast cancer, renal cancer, cancer in the digestive system, human melanoma, and combinations thereof.

13. The reagent according to claim 8, wherein said marker is selected from the group consisting of: enzymes, chromophors, chemoluminescent materials, radionucleotides, and combinations thereof.

* * * * *